United States Patent
Soini et al.

(12)

(10) Patent No.: US 6,342,397 B1
(45) Date of Patent: Jan. 29, 2002

(54) HOMOGENEOUS BIOSPECIFIC ASSAY USING A SOLID PHASE, TWO-PHOTON EXCITATION AND CONFOCAL FLUORESCENCE DETECTION

(75) Inventors: Erkki Soini, Krypingintie 20, FIN-21610 Kirjala; Pekka Hänninen, Turku, both of (FI)

(73) Assignee: Erkki Soini, Kirjala (FI)

( * ) Notice: Subject to any disclaimer, the term of this patent is extended or adjusted under 35 U.S.C. 154(b) by 0 days.

(21) Appl. No.: 09/699,635

(22) Filed: Oct. 31, 2000

Related U.S. Application Data

(63) Continuation of application No. PCT/FI99/00393, filed on May 11, 1999.

(30) Foreign Application Priority Data

Jun. 4, 1998 (FI) ............................................... 981272 U

(51) Int. Cl.[7] ........................ G01N 33/53; G01N 33/00; G01V 5/00; G01J 3/30
(52) U.S. Cl. ........................ 436/518; 436/172; 436/501; 436/513; 436/524; 436/536; 436/800; 422/68.1; 422/73; 422/82.05; 250/298; 250/396; 250/397; 250/458.1; 250/459.1; 250/461.1; 250/461.2; 356/4.01; 356/4.05; 356/73; 356/213; 356/317; 356/318; 356/336; 356/337; 356/341; 356/342; 356/441; 356/442; 435/7.1
(58) Field of Search ................................ 356/4.01, 4.05, 356/430, 336, 337, 341, 342, 318, 945; 250/458.1, 396, 397, 398, 459.1, 461.1, 461.2; 436/501, 513, 518, 524, 536, 800, 172; 435/7.1

(56) References Cited

U.S. PATENT DOCUMENTS

| | | | |
|---|---|---|---|
| 4,804,625 A | * | 2/1989 | Morrison et al. ............. 435/7 |
| 4,977,077 A | | 12/1990 | Ngo et al. |
| 5,028,545 A | * | 7/1991 | Soini ........................... 436/501 |
| 5,274,240 A | * | 12/1993 | Mathies et al. .......... 250/458.1 |
| 5,518,883 A | * | 5/1996 | Soini ............................... 435/6 |
| 5,777,732 A | * | 7/1998 | Hanninen et al. ........... 356/318 |
| 5,891,738 A | * | 4/1999 | Soini et al. .................. 436/501 |
| 6,020,591 A | * | 2/2000 | Harter et al. ............. 250/458.1 |
| 6,177,190 B1 | * | 1/2001 | Kain et al. .................. 356/246 |
| 6,177,277 B1 | * | 1/2001 | Soini ............................ 436/63 |
| 6,207,960 B1 | * | 3/2001 | Stern ....................... 250/458.1 |
| 6,210,973 B1 | * | 4/2001 | Pettit ............................ 436/172 |

FOREIGN PATENT DOCUMENTS

| | | | |
|---|---|---|---|
| EP | 0 296 136 A1 | * | 12/1988 |
| EP | 0 723 146 | | 9/1993 |
| EP | 0 666 473 | | 8/1995 |
| WO | WO 94/01774 | * | 1/1994 |
| WO | WO 94/11735 A1 | * | 5/1994 |
| WO | WO 96/22521 A1 | * | 7/1996 |
| WO | WO 96/22531 | | 7/1996 |
| WO | WO 96/27798 | | 12/1996 |

* cited by examiner

*Primary Examiner*—Long V. Le
*Assistant Examiner*—Kartic Padmanabhan
(74) *Attorney, Agent, or Firm*—James C. Lydon

(57) ABSTRACT

A homogeneous biospecific assay method for an analyte in solution or in a biological suspension, in which a biospecific reagent competitively binding an analyte and a ligand labeled with a fluorescent molecule, is reacted with and bound to a solid phase, and in which the free labeled ligand is extracted is excited with two-photon excitation by focusing a laser beam suitable for two-photon excitation into the sample volume; and the concentration of the analyte is calculated based on the photon emission contributed by the free labeled ligand.

9 Claims, 2 Drawing Sheets

HOMOGENEOUS BIOSPECIFIC ASSAY USING A SOLID PHASE, TWO-PHOTON EXCITATION AND CONFOCAL FLUORESCENCE DETECTION

This application is a continuation of Internationalj Application PCT/FI99/00393, filed on May 11, 1999 and published in the English language on Dec. 9, 1999.

BACKGROUND OF THE INVENTION

Bioaffinity assay methods are commonly used in the analytics of various biologically active molecules. Different applications of these methods are widely used in routine diagnostics and research laboratories. The most commonly used bioaffinity assay methods are immunoassays in which antigens serve as biospecific reagents.

The method of this invention refers to fluorometric bioaffinity assays in which the first biospecific reagent Ab (for example, a protein, antibody, nucleotide) is bound to a solid reaction matrix, which may be, for example, the inner wall of a reaction cuvette or microparticle suspension. Components bound to the reaction matrix are later referred to as solid phase. Another biospecific reagent, which is later referred to as ligand (biologically active molecule such as a steroid or other hormone, drug or oligonucleotide), is labelled with a fluorescent label. This reagent is later simply referred to as label. The assay method of this invention is a so called compentitive assay in which a reagent bound to the solid matrix has affinity both to an analyte and labelled ligand.

The competitive assay method of this invention is particularly suitable for small analyte molecules Ag. Characteristic to the competitive method is that the concentrations of the reaction components are adjusted so that the concentration of the biospecific reagent Ab is typically lower than that of the analyte and labelled ligand and the type of the assay is also called as limited reagent assay. Labelled ligand Ag* may be the same molecule as analyte molecule Ag, or it may be another molecule containing a corresponding affinity determinant such as Ag. Since the concentration of reagent Ab is lower than that of other components in the reaction solution, components Ag and Ag* bind to reagent Ab of the solid phase in their proportional concentrations. This is therefore called competitive binding. A standard curve of this assay is non-linear (sigmoidal). The standard curve refers to a graph obtained from calibration measurements. The graph presents dependence of signal response (fluorescence intensity) on analyte concentration.

A problem with conventional assay and research methods lies in their complexity. For example, the determination of hormons from blood with a competitive fluorometric immunoassay method requires several steps as follows: separation of cells from the serum, dispensing and dilution of the serum sample, addition of the labelled reagent, incubation, separation of the free fraction by washing, addition of the measurement solution and measurement of the signal. The majority of known measuring devices require at least 10–100 microliter reaction volumes. The separation step is very difficult to perform reliably if the reaction volume is less than 10 microliter.

There is a constant need for simpler microvolume and more cost-effective assays for routine diagnostics. In practice, this means a single step assay method with liquid volumes only a fraction of volumes of current assays. The new fluorometric biospecific assay method of this invention is a single step method, it does not require separation of the label and suits well for assaying very small samples, which may be either solutions or cell suspensions. In the method according to this invention, the signal strength is also independent of a sample size, and the smallest possible sample size depends only on the available liquid handling techniques.

BRIEF SUMMARY OF THE INVENTION

An example of computer simulation of a typical assay has been presented in FIG. 1 and FIG. 2. The method according to this invention can be performed for example as follows:

A solid phase is prepared in advance. The solid phase is coated with biospecific reagent Ab which binds said analyte and ligand. The solid phase may be located either on the inner wall of the reaction cuvette, or on the surface of the microparticles added to the reaction volume.

A ligand is labelled with a fluorescent molecule.

The sample to be determined and the labelled ligand Ag* is added into the reaction cuvette as such or with the microparticle suspension; and due to bioaffinity, analyte molecules Ag and labelled ligands Ag* start to bind competitively to reagent molecules residing on the surface of the solid phase.

A laser beam is focused through an objective lens into the liquid in the cuvette. The parameters of the laser beam and the numerical aperture of the lens are selected so that the focal volume of the laser beam is significantly smaller than the volume of the cuvette; and in practice limited by diffraction. Moreover, the laser wavelength and the intensity is selected to generate two-photon excitation in the fluorescent molecules of the solution. The excited states of the fluorescent molecules will relax with a specific fluorescence decay rate, emitting photons which are detected with a appropriate photon detector. The signal strength obtained from the detector or the single photon count rate is directly proportional to the concentration of fluorescent labels in the solution.

The less analyte there is in the solution the more fluorescent label is bound to the solid phase. It is possible, therefore, on the basis of the calibration and the signal obtained from the label, to determine the concentration of the analyte in the solution.

DETAILED DESCRIPTION OF THE PREFERRED EMBODIMENTS

Figure 1:
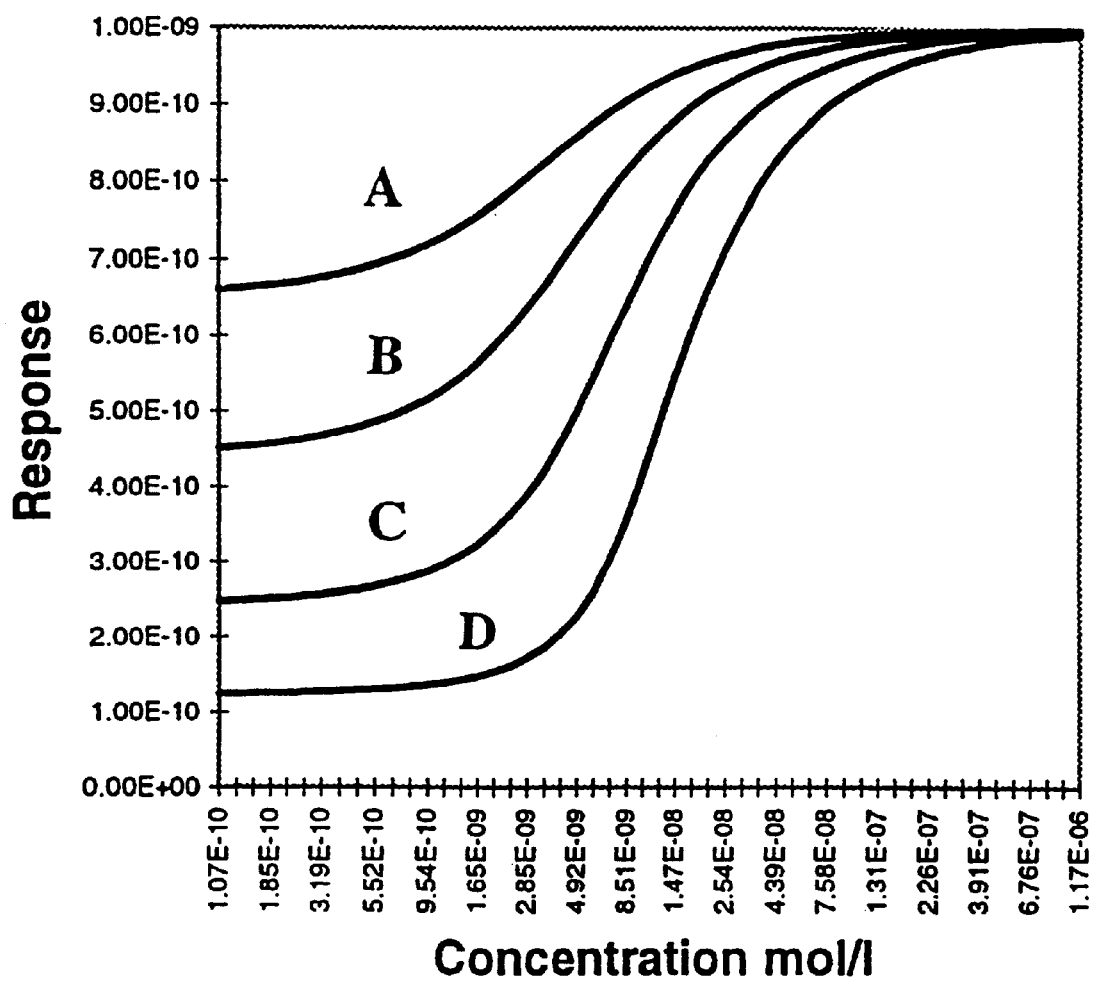
FIG. 1 is a plot of fluorescent response against time dependent concentration of labeled analyte Ag* concentration for four concentrations: Curve A for $1 \times 10^{-9}$ mol/L, Curve B for $2 \times 10^{-9}$ mol/L, Curve C for $4 \times 10^{-9}$ mol/L, and Curve D for $8 \times 10^{-9}$ mol/L.

In the method above, the optical system used for focusing the laser and detecting signals is based on two-photon excitation. Two-photon excitation generates excited states only in a restricted focal volume which is determined by the point spread function of the two-photon excitation focal point. This focal volume is very small, typically under 1 femtoliter or it can be expanded up to 10 femtoliters or even more by choosing appropriate optical parameters. Factors determining the focal volume are explained later in this text. When the focal volume of the laser beam is set to the centre of the liquid volume of the cuvette, the laser beam can not produce fluorescent excitation outside the focal volume, i.e. in the solid phase, elasewhere in the solution or in the optics because the focal volume is highly restricted. Microparticles randomly floating into the focal volume emit a signal during the short period that they reside under the influence of the laser beam in the focal volume. These signals can, however, be electronically rejected, since they emit a clear signal to a microparticle detector. A microparticle detector refers to a component detecting the microparticles which float into the focal volume. A microparticle detector may be, for example, a traditional light scattering detector. It can also be a photon detector which detects the fluorescence signal of a dye bound to the microparticle surface or located inside the microparticle. Said light sacattering or fluorescence are excited either with a separate light source or with the same laser used for two-photon excitation. The light scattering or fluorescence signal are detected either in visible or near infra red (NIR) range of the spectrum, and the excitation-detection system may also be confocal.

It is known that the background signal caused by scattering and auto-fluorescence can be eliminated using two-photon excitation (FI 90175, FI 951040 and WO 9622531). It is also known that two-photon excitation makes it possible to restrict the detection of the fluorescence emission to a very small, even under 1 femtoliter diffraction limited volume.

An essential discovery leading to this invention was that, by using an advanced two-photon excitation/detection concept we managed to design a surprisingly sensitive measuring system for diluted fluorescent solutions. Its sensitivity is sufficient for the method explained above. Unlike earlier methods described in FI 90175, FI 951040 and WO 9622531, the method of this invention measures concentration of the fluorescent ligands in the solution and reduction of the concentration as the ligands bind to the solid phase. In the method of this invention, signals generated by two-photon excitation are registered only when there are free labelled ligands in the focal volume, which are evenly spread throughout the solution. Labelled ligands bound to the solid hase and residing outside the focal volume do not emit a signal, because the two-photon detection is sharply restricted in volume. A solid phase outsie the diffraction limited focal volume does not contribute a signal, although it is in the same measuring cuvette. This permits competitive bioaffinity assays without the need for a separation step. In literature, this type of an assay is called as homogenous assay. Thus, the most important discovery of this invention is the volume restricted detection of the ligand concentration in the solution.

In the method of this invention the separation of signals emitted from the bound and the free labelled ligand is based on the fact that the two-photon excitation of fluorescence takes place only in the diffraction limited focal volume of the laser beam, which is typically about 1 femtoliter, and no excitation takes place outside the focal volume. Factors affecting the focal volume depend primarily on the numerical aperture of the objective lens and in addition on the intensity profile of the laser beam before the objective lens pupil. By selecting a smaller numeric aperture or a Gaussian profile instead of an even laser beam profile, focal volume can be enlarged. Simultaneously, however, the two-photon excitation efficiency will be reduced. Because of the non-linear nature of two-photon excitation, the intensity of fluorescence is also reduced although there is room for more labelled molecules in the focal volume. It is possible, however, to compensate this signal reduction by increasing the average power of the laser correspondingly. The most optimal way to increase the average power is to increase the laser pulse rate because the highest possible pulse peak power is limited by photolysis ("bleaching") and saturation of labels in the focal volume.

The solid phase may be bound to a cuvette wall or on the surface of the microparticles. Microparticles may be, for example, latex microparticles or biological particles. The light absorption of the said particles is minimal or non-existent in the NIR-wavelength of the laser beam used for two-photon excitation, which in pratice may be, for example, 1064 mm. The intensity of the light scattering of these particles depends on the relative refraction index. Scattering is more intense with latex-particles than with biological particles (for example, cells). Signals of latex-particles can be separated from signals emitted from other particles either through scattering or through signals emitted by a fluorescent dye attached to these particles. In some cases, it may be useful if these latex-particles are made of a material with a lower density than that of the solution. In such cases, the particles will gradually float towards the surface during the reaction, and simultaneously physically transport the solid phase away from the focal volume. Another possibiliy is to use magnetic particles which can, by using a magnetic field, be displaced from the focal zone of the laser.

In the method of this invention, the laser beam used in fluorescence excitation is focused directly into the reaction solution through a transparent wall in the reaction cuvette. A fluorescence signal from the solution is obtained for each laser pulse, and the registration of signals is discontinued once a microparticle used as a solid phase in and out of the focal volume either due to diffusion or liquid movement. Microparticles contribute a signal with an amplitude which is directly proportional to the amount of labelled complexes bound to the microparticle. Additionally, by registering these signals obtained from the microparticles, it is possible to analyse the signal obtained from the label bound to the solid phase besides the signal obtained from the free label. This may be useful, for example, for obtaining better measuring precision.

Due to the characteristics presented above, this method makes a fast, single step biospecific assays possible, for example, from liquids and cell suspensions, without the need for separation. Blood cells, for example, are totally transparent at the infrared illumination wavelength as used in this method of this invention. Consequently an assay in diluted whole blood can be performed which means a significant simplification of the present day's routine.

Since the measuring volume, in principle, equals the focal volume of the two-photon excitation, the fluorescence measuring concept of this invention does not require sample volumes larger than that of the focal volume. Thus one of the most important advantages of this method is that it allows samples in liquid volumes of one microliter or less without sacrificing sensitivity or measuring precision. This is especially important in screening of pharmaceutical substances. In practice, the sample size must be at least of such a volume that the liquids in question can be transferred accurately into the reaction cuvette. With traditional automatic dispensers, it is possible to transfer 5–10 microliter samples. Much smaller liquid volumes, 1 nanoliter–1 microliter, require new pietzo dispensers.

Two-photon Excitation

Two-photon excitation is created when, by focusing an intensive light source, the density of photons per unit volume and per unit time becomes high enough for two-photons to be absorbed into the same dye molecule. In this case, the absorbed energy is the sum of the energies of the two photons. According to the concepts of probability, the absorption of a single photon in a dye, is an independent event, and the absorption of several photons is a series of single, independent events. The probability of absorption of a single photon can be described as a linear function as long as the energy states that are to be excited are not saturated. The absorption of two photons is a non-linear process. In two-photon excitation, due molecules are excited only when both photons are absorbed simultaneously. The probability of absorption of two photons is equal to the product of probability distributions of absorption of the single photons. The emission of two photons is a thus a quadratic process.

The properties of the optical system used for the excitation of fluorescent dye can be described with the response of the system to a point-like light source. A point-like light source forms, due to diffraction, an intensity distribution in the focal point characteristic to the optical system (point spread function). When normalised, this intensity distribution is the probability distribution of how the photons from the point light source reach the focal area. In two-photon excitation, the probability distribution of excitation equals the normalised product of intensity distributions of the two photons. The probability distribution thus derived is, in the 3-dimensional space, especially the axial (depth) direction, clearly more restricted than the probability distribution of a single photon. Thus in two-photon excitation, only the fluorescence that is formed in the clearly restricted 3-dimensional vicinity—which is also called the focal volume-13 is excited.

When a dye is two-photon excited, the scattering of light in the vicinity of the focal point and from the optical components, is reduced remarkably compared to normal excitation. Furthermore, two-photon excitation decreases the background fluorescence outside the focal point, in the surroundings of the sample and in the optics. Since the exciting light beam must be focused onto as a small point as possible, two-photon excitation is most suitable for the analysis of small sample volumes, which is also the case in the method according to this invention. The advantage of two-photon excitation is also basd on the fact that visible or near-infrared (NIR) light, for example, can also be used for excitation in the ultraviolet or blue region. Similarly, excitation in the visible region can be achieved by NIR or IR light. Because the wavelength of the light source is considerably longer than the emission wavelength of the dye, the scattering at a wavelength of the light source and the possible autofluorescence is not generated or it can be effectively attenuated by using low-pass filters (attenuation of at least 10 orders of magnitude) to prevent them from reaching the detector. The light absorption of red cells in the NIR-range is very small. We have also discovered that the excitation light, for example, at 1064 nm wavelength does not induce fluorescence of hematoporphyrines, and therefore the background fluorescence caused by red cells is not significant even when the microparticle suspension contains a remarkable amount of red cells. Most often two-photon excitation requires laser equipment capable of producing ultra-short, high-energy pulses. In our experiments, we have observed that a very high signal-to-background-ratio and a good sensitivity can be reached with two-photon excitation and short-lived fluorescent labels by using low price microchip lasers with nanosecond pulse duration. Suitable fluorescent labels for two-photon excitation are, for example, BODIPY and rhodamine derivatives.

Example About Measuring Sensitivity

The literature describes confocal measuring systems with which it is possible to attain a similar point spread function as with two-photon excitation. The disadvantage of two-photon excitation compared to confocal systems is its lower signal intensity. Two-photon exciation possesses, however, many advantages, of which the most important are the absence of scattering background and lower autofluorescence. We performed comparative measurements with the equipment at our disposal, and discovered that with a 1 nmol/L rhodamine solution the signal-background ratio was 1000 with a two-photon system whereas it was 7 with a confocal system.

An Example

Using a methematical model, the reaction kinetics, and the consumption and production of different reaction components have been simulated, varying all possible reaction parameters. The reaction scheme of the assay of this example shows how the reaction between Ab and Ag produces complexes AbAg $$Ab + Ag \underset{\Leftarrow k_2}{\overset{k_1 \Rightarrow}{\longrightarrow}} AbAg \qquad (1)$$

where
$k_1$=association rate constant [L mol$^{-1}$s$^{-1}$] and
$k_2$=dissociation rate constant [s$^{-1}$]The reaction between Ab and Ag* produces complexes AbAg* and $$Ab + Ag^* \underset{\Leftarrow k_4}{\overset{k_3 \Rightarrow}{\longrightarrow}} AbAg^* \qquad (2)$$

where
$k_3$=association rate constant [L mol$^{-1}$s$^{-1}$] and
$k_4$=dissociation rate constant [s$^{-1}$]
(3) $K_1 = k_1/k_2$=reaction equilibrium constant (affinity) for Ag [L/mol]
(4) $K_3 = k_3/k_4$=reaction equilibrium constant (affinity) for Ag* [L/mol]

The reactions can be expressed with the following differential equations
(5) $dx_1/dt = -k_1 x_1 x_3 + k_2 x_4$
(6) $dx_2/dt = -k_3 x_2 x_3 + k_4 x_5$
(7) $dx_3/dt = -k_1 x_1 x_3 - k_3 x_2 x_3 + k_2 x_4 + k_4 x_5$
(8) $dx_4/dt = -k_2 x_4 + k_1 x_1 x_3$
(9) $dx_5/dt = -k_4 x_5 + k_3 x_2 x_3$
where
[Ag]=$x_1$
[Ag*]=$x_2$
[Ab]=$x_3$
[AgAb]=$x_4$
[Ag*Ab]=$x_5$
[Ab]=time dependent concentration of antibody [mol/L]
[Ag]=time dependent concentration of antigen [mol/L]
[Ag*]=time dependent concentration of labelled antigen [mol/L]
[AbAg]=time dependent concentration of antigen-antibody complex [mol/L]
[AbAg*]=time dependent concentration of labelled antigen-antibody complex [mol/L]

$[x]$=mol L$^{-1}$ [dx/dt]=mol L$^{-1}$s$^{-1}$ [k$_1$]=L mol$^{-1}$s$^{-1}$ [k$_2$]=s$^{-1}$ The initial mass of Ag, Ag* and Ab will be conserved in the reaction and therefore

(11) p=x$_1$+x$_4$
(12) p*=x$_2$+x$_5$
(13) q=x$_3$+x$_4$+x$_5$ where
p=initial Ag concentration,
p*=initial Ag* concentration and
q=initial Ab concentration The differential equations (Eqns. 6–10) and their solution describes the reaction kinetics. The solution of these differential equations can be easily calculated numerically and for the solution we used the adapted Runge-Kutta method provided by Mathcad 6.0+ mathematics program (Matsoft Inc., Cambridge, Mass., USA).

In this context we have chosen a practical example for modelling by using following initial concentrations: The initial concentration of the analyte Ag in the reactgion suspension varies from p=1·10$^{-10}$ mol/L to p=1·10$^{-6}$ mol/L, the equivalent concentration of the solid phase reagent Ab as related to the reaction volume is q=1·10$^{-9}$ mol/L and the initial concentration of the labelled ligand Ag* is p*=1·10$^9$ mol/L. Equilibrium constants of the biospecific reagents Ab and Ab* (affinity constants) are K=1·10$^9$ L/mol. The association rate constant between the analyte and the solid phase is k$_1$=1·10$^7$ L mol$^{-1}$s$^{-1}$ and that between the labelled ligand and solid phase is k$_2$=1·10$^7$ L mol$^{-1}$s$^{-1}$. It has also been assumed that the labelled ligand is 100% pure of the free label. It is obvious that a high purity can be obtained by the use of ordinary chromatographic methods because both the label and the ligand have a relative low molecular weight.

Figure 2:
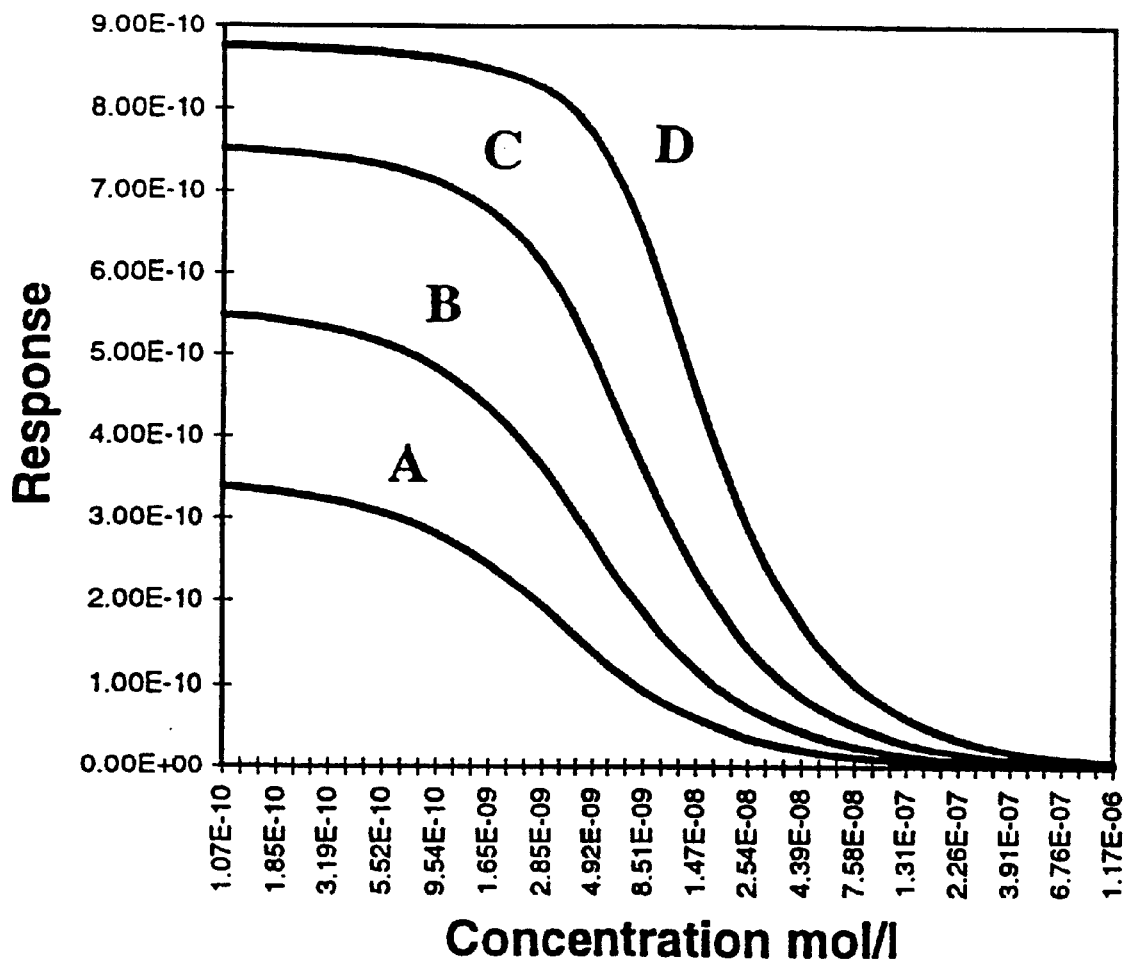
FIG. 2 is a plot of fluorescent response against time dependent concentration of labeled antigen-antibody AbAg* complex for four concentrations: Curve A for $1 \times 10^{-9}$ mol/L, Curve B for $2 \times 10^{-9}$ mol/L, Curve C for $4 \times 10^{-9}$ mol/L, and Curve D for $8 \times 10^{-9}$ mol/L.

FIG. 1 and FIG. 2 show standard curves of the assay for overnight incubation time. The abscissa is the concentration of the analyte (mol/L). FIG. 1 shows the standard curve for [Ag*] (mol/L). FIG. 2 shows the standard curve for [Ag*AB] (mol/L). Four different curves have been shown in both cases for different solid phase concentrations: curve A for 1·10$^{-9}$ mol/L, curve B for 1·10$^{-9}$ mol/L, curve C for 4·10$^{-9}$ mol/L, curve D for 8·10$^{-9}$ $^{mol/L}$.

It can be seen from these standard curves that it is advantageous to use a solid phase reagent Ab with capacity and concentration which is even higher than the concentration of the labelled ligand. Higher solid phase capacity provides stronger response effect when the analyte Ag concentration exceeds certain threshold value.

It can be seen from these standard curves that the method according to this invention is particularly suitable for screening assays, i.e, the assays where the quantitative value plays of lesser importance and purpose of the assay is to classify the samples in the simplest case in two categories only: positive and negative.

General

The method according to this invention and the necessary equipment can be realised in many different ways. However, an essential observation of this invention is that by directly focusing the laser beam on the reaction suspension, and by measuring the concentration of the free labelled ligand in the solution, the progress of the reaction can be followed either as a kinetic measurement or as an end point measurement. The concentration of a free label in the solution decreases as it binds to the solid phase. The fluorescence detector can be activated only for the short period of the laser pulse used for two-photon excitation which means that photon emissions and thermal noise which occur between excitation intervals are not measured. Simultaneously, the photon detector can be inactivated at the very moment the microparticle hits the focal volume. Information about the position of microparticles at the focal volume is obtained, for example, through scattering at the laser beam wavelength, or through fluorescence bound to the particles. The best way to measure scattering is to use a confocal scattering detector. Scattering signal from blood cells is orders of magnitude weaker, because their relative refraction index is much lower than that of latex-microparticles. Scattering and background fluorescence caused by cells can be further minimized by perforating cell membranes with isotonic solution and as a result, intracellular fluid and haemoglobin and its fluorescent porphyrin compounds are diluted in the assay suspension.

A specialist in the field appreciates that the different embodiments of the said invention may vary within the scope of the claims presented in the following section.

What is claimed is:

1. A homogeneous biospecific assay method, comprising a) adding a ligand labeled with a fluorescent molecule to a sample comprising an analyte in a solution or in a biological suspension;

b) adding a biospecific reagent to said sample, wherein said biospecific reagent is bound to a solid support which is either an inner surface of a cuvette containing said sample or said support comprises microparticles suspended in said sample, and wherein said biospecific reagent will competitively bind to said analyte and said ligand;

c) creating a diffraction limited, two-photon excitation focal volume within said sample using a laser focused through an objective lens;

d) exciting a free labeled ligand within said focal volume by two-photon fluorescence excitation;

e) detecting photon emission from said focal volume during a time when there is no solid phase within or adjacent said focal volume;

f) calculating a concentration of analyte in said sample based on said detected photon emission from said free labeled ligand.

2. The method of claim 1, wherein said solid phase is bound to said inner surface of a cuvette.

3. The method of claim 2, wherein said focal volume is not focused on a labeled reagent bound to said solid phase.

4. The method of claim 1, wherein said solid phase comprises microparticles suspended in said sample.

5. The method of claim 4, wherein detection of photon emission is interrupted when a microparticle floats into said focal volume.

6. The method of claim 5, further comprising detecting light scattering at a wavelength of said laser to obtain information about a position of microparticles in a vicinity of said focal volume.

7. The method of claim 6, wherein a confocal scattering detector is used to detect light scattering.

8. The method of claim 5, further comprising detecting a signal emitted from a fluorescent dye bound to said microparticles to obtain information about a position of microparticles in a vicinity of said focal volume.

9. The method of claim 6, wherein a confocal fluorescence detector is used to detect said signal.

* * * * *